United States Patent
Blin (10) Patent No.: US 11,083,826 B2
(45) Date of Patent: Aug. 10, 2021

(54) DEVICE FOR CONTROLLING A BLOOD FLOW PRODUCED IN A HEMORRHAGIC AREA

(71) Applicants: UNIVERSITÉ GRENOBLE ALPES, Saint-Martin-d'Hères (FR); CENTRE HOSPITALIER UNIVERSITAIRE DE GRENOBLE, Grenoble (FR)

(72) Inventor: Dominique Blin, La Tronche (FR)

(73) Assignee: HEMOSQUID, Saint Martin d'Heres (FR)

( * ) Notice: Subject to any disclaimer, the term of this patent is extended or adjusted under 35 U.S.C. 154(b) by 414 days.

(21) Appl. No.: 15/892,731

(22) Filed: Feb. 9, 2018

(65) Prior Publication Data
US 2018/0161485 A1 Jun. 14, 2018

Related U.S. Application Data

(62) Division of application No. 13/810,026, filed as application No. PCT/FR2011/051689 on Jul. 13, 2011, now Pat. No. 9,919,083.

(30) Foreign Application Priority Data

Jul. 13, 2010 (FR) ..................... 10/55736

(51) Int. Cl.
*A61M 1/00* (2006.01)
*A61B 17/12* (2006.01)
(Continued)

(52) U.S. Cl.
CPC ........... *A61M 1/0088* (2013.01); *A61B 17/08* (2013.01); *A61B 17/12* (2013.01);
(Continued)

(58) Field of Classification Search
CPC .............. A61M 1/0088; A61M 1/0023; A61M 1/0058; A61M 1/006; A61M 1/0062;
(Continued)

(56) References Cited

U.S. PATENT DOCUMENTS 3,896,810 A 7/1975 Akiyama
4,633,865 A 1/1987 Hengstberger et al.
(Continued)

FOREIGN PATENT DOCUMENTS

WO 9838944 9/1998
WO 2006012992 2/2006
(Continued)

OTHER PUBLICATIONS

International Search Report, dated Nov. 11, 2011, from corresponding PCT application.

*Primary Examiner* — Melanie R Tyson
*Assistant Examiner* — Chima U Igboko
(74) *Attorney, Agent, or Firm* — Nixon & Vanderhye (57) ABSTRACT

A device for controlling blood flow occurring in a haemorrhagic zone of a biological tissue, includes a flexible plate arranged to be placed opposite this zone, the flexible plate including: substantially leaktight peripheral supporting elements, for applying on the tissue so that the zone is surrounded; a back wall delimiting, with the supporting elements, opposite the zone, a hollow space; connecting elements connecting the hollow space, externally to the flexible plate, to an external aspiration source for creating a vacuum in the hollow space for aspirating and tightly applying the surface of the tissue against the peripheral supporting elements; and a hollow stud placed between the zone and the back wall and hollowed out in its centre on the side of the zone along an axis substantially perpendicular to (Continued)

the back wall, and arranged to be in contact with the zone when the vacuum is created in the space.

7 Claims, 6 Drawing Sheets

(51) Int. Cl.
| | | |
|---|---|---|
| *A61B 17/42* | (2006.01) | |
| *A61B 17/08* | (2006.01) | |
| *A61B 17/00* | (2006.01) | |
| *A61B 17/30* | (2006.01) | |
| *A61M 27/00* | (2006.01) | |
| *A61B 90/00* | (2016.01) | |

(52) U.S. Cl.
CPC ........ *A61B 17/12022* (2013.01); *A61B 17/42* (2013.01); *A61B 17/00491* (2013.01); *A61B 17/12013* (2013.01); *A61B 90/361* (2016.02); *A61B 2017/00884* (2013.01); *A61B 2017/00889* (2013.01); *A61B 2017/00893* (2013.01); *A61B 2017/12004* (2013.01); *A61B 2017/306* (2013.01); *A61B 2017/308* (2013.01); *A61B 2017/4216* (2013.01); *A61M 27/00* (2013.01)

(58) Field of Classification Search
CPC .. A61M 1/008; A61M 1/0082; A61M 1/0084; A61M 1/0086; A61M 1/0092; A61M 27/00; A61B 17/08; A61B 17/42; A61B 17/12022; A61B 17/12; A61B 2017/4216; A61B 2017/308; A61B 2017/306; A61B 2017/00884

See application file for complete search history.

(56) References Cited

U.S. PATENT DOCUMENTS

| | | |
|---|---|---|
| 5,906,607 A | 5/1999 | Taylor et al. |
| 6,436,113 B1 | 8/2002 | Burba et al. |
| 6,558,314 B1 | 5/2003 | Adelman et al. |
| 6,641,604 B1 | 11/2003 | Adelman et al. |
| 2003/0139646 A1 | 7/2003 | Sharrow et al. |
| 2004/0254431 A1* | 12/2004 | Necola Shehada .. A61B 5/0075 600/327 |
| 2007/0265585 A1 | 11/2007 | Joshi et al. |
| 2007/0282310 A1* | 12/2007 | Bengtson ............... A61M 27/00 604/543 |
| 2011/0066178 A1 | 3/2011 | Blin |
| 2011/0282337 A1* | 11/2011 | Hall ................. A61B 17/32002 606/33 |

FOREIGN PATENT DOCUMENTS

| | | |
|---|---|---|
| WO | 2009101348 | 8/2009 |
| WO | 2010053463 | 5/2010 |

* cited by examiner

DEVICE FOR CONTROLLING A BLOOD FLOW PRODUCED IN A HEMORRHAGIC AREA

FIELD OF TECHNOLOGY

The present invention relates to a device for controlling a blood flow occurring in a hemorrhagic zone, in particular in a point zone (the largest diameter of which is less than about 10 mm) of the human or more generally animal body.

Such a device for example enables a user to control and stop a large blood flow occurring:
- in a highly vascularized zone of biological tissue, in particular belonging to a natural internal cavity of a patient's body and which consequently is difficult to access, said blood flow creating a severe hemorrhage in this zone;
- after a vascular wound, whether during surgery or after an injury. This flow may be located in a deep region, difficult of access, in a natural cavity such as the stomach or the uterus. This bleeding may be impossible to reach directly, as in video-surgery. The device according to the invention represents an addition to the conventional techniques of hemostasis, which may be ineffective in such circumstances.

STATE OF THE PRIOR ART

A hemostasis device is already known (see for example patent application WO2009101348) for controlling and stopping a blood flow, by carrying out, at the level of a wound or against an exposed, directly accessible tissue area, drainage by aspiration, which causes evacuation of dead particles, which may or may not be infected, and some migration of tissues promoting this hemostasis.

A first technical problem arising in the light of the prior art is proper holding of such a device against said wound or said tissue.

A second technical problem arising in the light of the prior art is that of holding together two opposite walls of a "hollow" organ for example the uterus in the case of hemorrhages that may occur in the inside wall of the uterus during delivery in childbirth.

The purpose of the invention is to solve said first or second problem.

DISCLOSURE OF THE INVENTION

The first problem is solved with a device for controlling a blood flow occurring in a hemorrhagic zone of a biological tissue, comprising a flexible plate, this plate being arranged to be placed opposite this zone, said flexible plate comprising:
- peripheral supporting means, substantially leaktight, suitable for being applied on the biological tissue so that the hemorrhagic zone is surrounded,
- a back wall, said back wall delimiting with the supporting means, opposite the zone, a hollow space, and
- connecting means arranged for connecting the hollow space, externally to the flexible plate, to an external aspiration source for creating a vacuum in the hollow space for aspirating and tightly applying the surface of the tissue against the peripheral supporting means, characterized in that it further comprises a hollow stud placed between the zone and the back wall and hollowed out in its center on the zone side along an axis substantially perpendicular to the back wall, and arranged to be in contact with the zone when the vacuum is created in the space.

The hollow stud can be arranged so that, when its hollowed-out side is in contact with the zone, it is isolated from the vacuum created in the space.

The hollow stud need not comprise a hole connecting its hollowed-out interior to the space.

The hollow stud can have a cylindrical shape with axis of symmetry substantially perpendicular to the back wall.

The hollow stud can be arranged to be filled with a product such as hemostatic adhesive or a hemostatic product.

The back wall can be arranged to be pierced by a syringe for injecting a product such as hemostatic adhesive or hemostatic product in the hollow stud without passing through the connecting means between the hollow space and the aspirating means.

The connecting means can be arranged for connecting the hollow space without an intermediate collecting housing arranged in the thickness of the back wall.

The hollow stud can be centered on the back wall.

The hollow stud can be arranged for receiving, on the zone side, a hollowed-out ring that surrounds the hollow stud so that the junction between the hollow stud and the ring is hermetic.

The device according to the invention can comprise a hollowed-out ring that surrounds the hollow stud on the zone side so that the junction between the hollow stud and the ring is hermetic.

The ring can have a cylindrical shape.

The ring can have a shape that is flared in the direction of the zone.

The device according to the invention can comprise a skirt placed between the peripheral supporting means and the hollow stud, surrounding the hollow stud, and arranged to be in contact with the zone when the vacuum is created in the space. The skirt can be centered on the back wall. The skirt can be equipped with teeth directed towards the zone and arranged to be in contact with the zone when the vacuum is created in the space.

The peripheral supporting means can be arranged for receiving an additional piece for altering the plate area or for modifying its profile.

The back wall can be leaktight and impermeable.

The device according to the invention can incorporate a camera for aiding in positioning the plate on the zone.

According to yet another aspect of the invention, the second problem is solved with a device for controlling a blood flow occurring in a hemorrhagic zone of a biological tissue, comprising:
- a flexible plate equipped with two opposite faces, said plate comprising an internal volume between its two faces, and
- connecting means arranged for connecting the internal volume to aspirating means external to said device so as to create negative pressure in this internal volume,
- each of the faces being provided with holes so that the internal volume and the exterior of the plate communicate through these faces.

Each of the faces of the plate can be provided, towards the exterior of the device, with patterns in relief.

The patterns can be distributed on the faces regularly, with a substantially constant surface density.

According to yet another aspect of the invention, a method is proposed for controlling a blood flow occurring in a biological closed space, in which the device according to the invention is placed on the hemorrhagic zone.

DESCRIPTION OF THE DRAWINGS AND EMBODIMENTS

Other advantages and features of the invention will become apparent on reading the detailed description of implementations and embodiments, which are in no way limitative, and the following attached drawings:

FIG. 6 is a profile sectional view of a first embodiment of the ring according to the invention for surrounding the hollow stud of the first or second embodiment of the device according to the invention, FIG. 7 is a profile sectional view of a second embodiment of the ring according to the invention for surrounding the hollow stud of the first or second embodiment of the device according to the invention, FIG. 8 is a profile sectional view of a variant of device according to the invention, each of FIGS. 9 to 11 is a profile sectional view of an additional piece for the first or second embodiment of the device according to the invention.

In general, the dimensions shown in the figures are in millimetres.

DETAILED DESCRIPTION OF THE INVENTION

Figure 1:
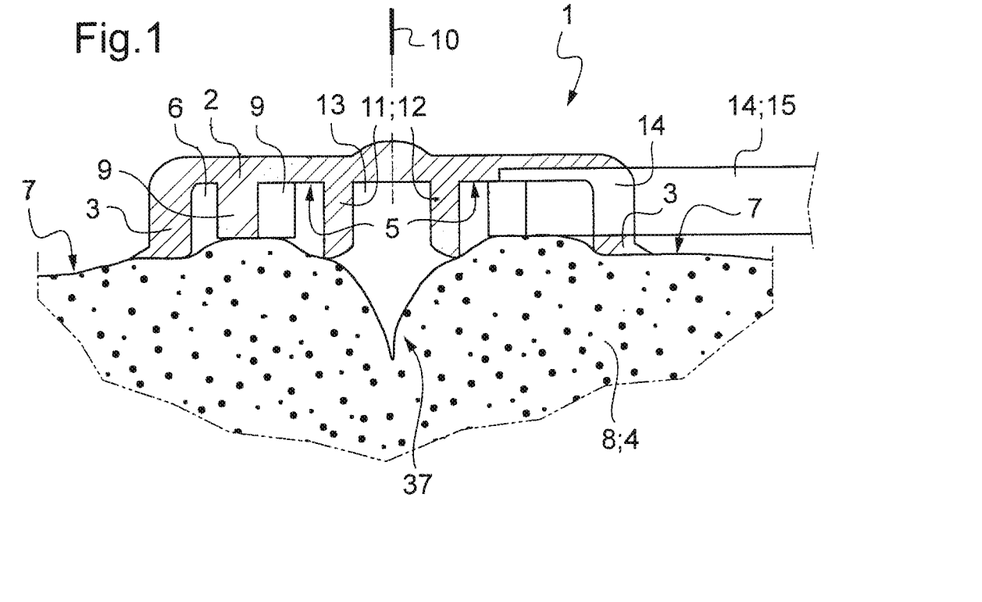
FIG. 1 is a profile sectional view of a first embodiment of the device according to the invention called "small plate"
Figure 2:
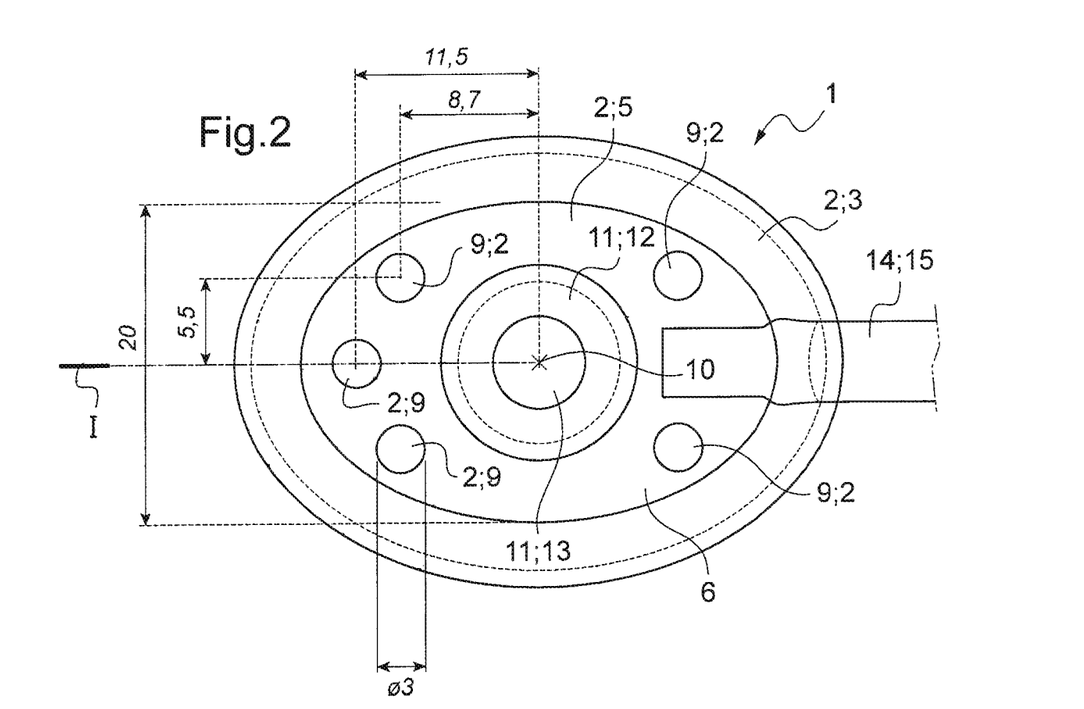
FIG. 2 is a bottom view of the first embodiment of the device according to the invention of FIG. 1.

A description will firstly be given, with reference to FIGS. 1 and 2, of a first embodiment of device "A1" (referenced 1 in the figures) according to the invention called "small plate".

FIG. 1 is a profile sectional view along axis I of FIG. 2.

The device 1, for controlling a blood flow occurring in a hemorrhagic zone 4 of a biological tissue 8, comprises a flat flexible plate 2.

Viewed from below or from above, the plate has a round or oval shape.

The flexible plate 2 is made of natural or synthetic rubber or of plastic material of the silicone type.

The flexible plate 2 comprises:
substantially leaktight peripheral supporting means 3,
a back wall 5,
connecting means 14 to an aspiration source external to the device (not shown),
a hollow stud 11.

The plate 2 is arranged to be placed opposite and to extend parallel to said hemorrhagic zone 4, so that:
the substantially leaktight peripheral supporting means 3 are applied on the biological tissue 8 so that the hemorrhagic zone 4 is surrounded,
the back wall 5 delimits, with the supporting means 3, opposite zone 4, a hollow space 6,
the connecting means 14 are arranged for connecting the hollow space 6, externally to the flexible plate 2, to the external aspiration source (not shown) to create a vacuum in hollow space 6 for aspirating and tightly applying the surface 7 of the tissue 8 against the peripheral supporting means 3, and
the hollow stud 11 is placed between zone 4 and the back wall 5 and is hollowed out in its center on the zone side 4 along an axis 10 substantially perpendicular to the back wall, and is arranged to be in contact with the zone 4 when the vacuum is created in the space 6.

The connecting means 14 comprise a tube 15 (or connecting duct) opening inside the hollow space 6.

As shown in FIGS. 1 and 2, the hollow stud 11 has a cylindrical shape with axis of symmetry 10 substantially perpendicular to the back wall 5.

Moreover, the hollow stud 11 is centered on the back wall 5.

The back wall 5 is leaktight and impermeable, just like the peripheral supporting means 3. By "impermeable" is meant that it isolates and does not allow a liquid or a pressure difference to be propagated through it.

The peripheral supporting means 3 of the flexible plate consist of a flexible rim surrounding the back wall 5 of this plate and integral with the latter.

The device 1 further comprises discontinuous inserts 9 arranged for stiffening the flexible plate 2, these inserts being placed between this zone 4 and the back wall 5.

The discontinuous inserts 9 are in addition intended to facilitate the propagation of the vacuum in the hollow space 6 and to limit sliding of the device according to the invention on the surface 7.

The discontinuous inserts 9 comprise studs 9 distributed on the back wall. The inserts consist of a plurality of bracing studs 9, preferably identical, equidistant and regularly distributed over the extent of the flexible plate 2, so that one of their ends comes into contact with the hemorrhagic zone, said studs 9 being integral with the back wall 5 at their opposite ends. The studs 9 have a solid cylindrical profile, of circular cross-section. The inserts 9 are made of the same material as the plate, namely of natural or synthetic rubber or of plastic of the silicone type.

Thus, the plate 2 of the device 1 forms a flat sucker having a leaktight covering, which can surround and be applied tightly against the wound 37 or zone 4 of the tissue 8 to be treated, the site of a hemorrhage or of a blood flow that is to be controlled, said sucker coming into contact with the periphery of zone 4 of the tissue 8 and delimiting an internal volume 6 connected hermetically by a catheter or a similar connecting tube 15 to an external aspirating and vacuuming device, creating negative pressure of a defined value in this volume 6, between the sucker and zone 4 of tissue 8.

Owing to these arrangements, the wound 37 closes up by migration of the tissues under the action of the negative pressure created, the internal supporting elements 9, 11 holding the tissue 8 substantially in place.

Figure 5:
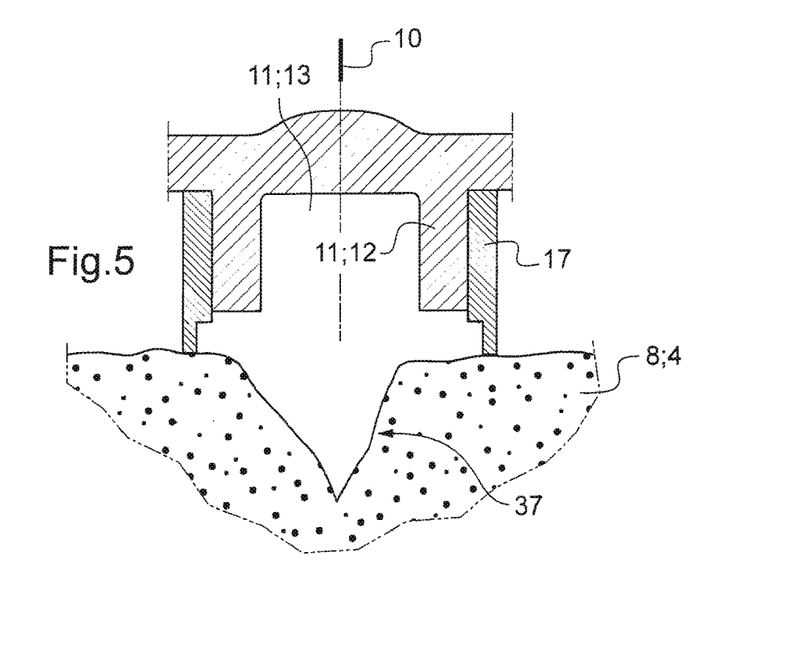
FIG. 5 is a profile sectional view of a hollow stud of the first or second embodiment of the device according to the invention.

The hollow stud 11 comprises a circumferential wall 12 surrounding a hollow interior 13. The wall 12 is leaktight. The hollow stud 11 is arranged so that when its hollowed-out side is in contact with the zone 4, its wall 12 surrounds the wound 37 so that the wound 37 is placed opposite the hollow interior 13.

The hollow stud 11 is arranged so that when its hollowed-out side is in contact with the zone 4, its hollow interior 13 is isolated from the vacuum created in the space 6. In particular, the hollow stud 11 does not comprise, in its wall 12, a hole connecting its hollowed-out interior 13 to the space 6.

The hollow stud 11 is arranged to be filled with hemostatic adhesive or hemostatic product, more precisely the hollow interior 13 is arranged to be filled with hemostatic adhesive or hemostatic product.

The back wall 5 is arranged to be pierced by a syringe (for example along axis 10, from the exterior of the device 1 to the hollow interior 13) for injecting hemostatic adhesive or hemostatic product in the hollow interior 13 of stud 11 without passing through the connecting means 14 between the hollow space 6 and the aspirating means. In particular, the connecting means 14 are arranged for connecting the hollow space 6 directly to the connecting duct 15 without an intermediate collecting housing arranged in the thickness of the back wall 5.

Thus, adhesive or a hemostatic product can be inserted in the hollow interior 13 to ensure that the device is held properly on the tissue 8, in particular good holding of the stud 11 on the wound 37, without risk of piercing the connecting means 14 to the aspirating means creating the vacuum, and without risk of the adhesive or hemostatic product being aspirated into the space 6 and then to the aspirating means.

In another variant, the adhesive or the hemostatic product is inserted beforehand in the hollow space 13, before the plate 2 is applied on the wound 37. Thus, adhesive or the hemostatic product can be inserted in the hollow interior 13 to ensure that the device is held properly on the tissue 8, in particular to ensure good holding of the stud 11 on the wound 37, without risk of the hemostatic adhesive being aspirated into the space 6 and then to the aspirating means.

It should be noted that a product other than adhesive can be inserted in the hollow interior, for example an adhesive, antiseptic, cicatrizant and/or antibiotic product.

The device 1 can for example be used:

for wounds with difficult access, in cavities where difficult access can make effective control of this hemorrhage by the traditional means uncertain, for example on the inside wall of a natural cavity such as the inside wall of the esophagus, of the alimentary canal in particular at the level of the stomach between the cardia and the duodenum, or even in the wall of the latter, of the peritoneum and of the intestine and in particular of the colon, in the case of a lesion or an open wound occurring on an organ the tissue of which is particularly fragile, such as the heart, liver or spleen, where control of the hemorrhage mainly requires not aspirating the blood flowing from the wound, but more immediately to bring the edges of the wound closer together smartly, keeping them applied against one another by a fixing effect following placement of the device, this effect closing up the lesion until the hemorrhage is suitably stopped, or to contain the bleeding in a closed space, in the case of so-called raw surfaces, created between two walls or biological membranes normally in close contact but accidentally separated from one another by cleavage, such as between the pleura and the wall of the lung, and between which bleeding or a diffuse hemorrhage occurs, which has to be controlled and stopped quickly.

A description will now be given, with reference to FIGS. 3 and 4, of a second embodiment of the device "A2" (referenced 16 in the figures) according to the invention called "large plate", only with respect to its differences relative to the first embodiment.

Figure 3:
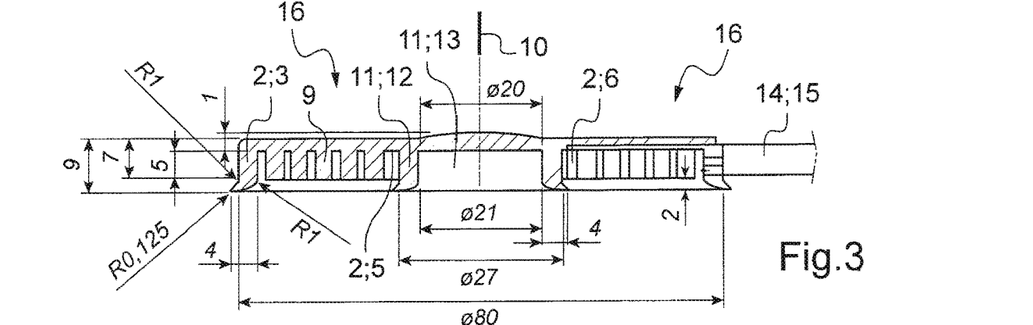
FIG. 3 is a profile sectional view of a second embodiment of the device according to the invention called "large plate"
Figure 4:
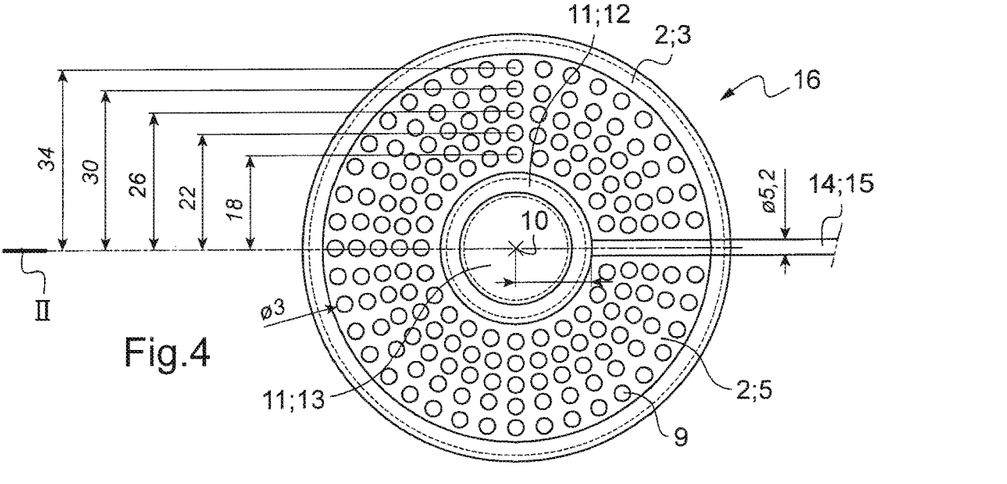
FIG. 4 is a bottom view of the second embodiment of the device according to the invention of FIG. 3.

FIG. 3 is a profile sectional view along axis II in FIG. 4.

This second embodiment is identical to the first embodiment, except that it is of larger dimensions and it comprises a larger number of studs 9.

A description will now be given, with reference to FIGS. 5 to 7, of a hollow stud 11 of the first or second embodiment of the device according to the invention, and various embodiments of rings associated with this hollow stud 11.

In the first and second embodiments of the device according to the invention, the hollow stud 11 is arranged for receiving, on the zone side 4 (i.e. on its hollowed-out side), a hollowed-out detachable ring 17 surrounding the hollow stud 11 so that the junction between the hollow stud 11 and the ring 17 is hermetic.

The device 1, 16 therefore typically comprises a hollowed-out ring that surrounds the hollow stud 11 on the zone side 4 so that the junction between the hollow stud 11 and the ring is hermetic.

Figures 6, 7, 8, 9, 10, 11:
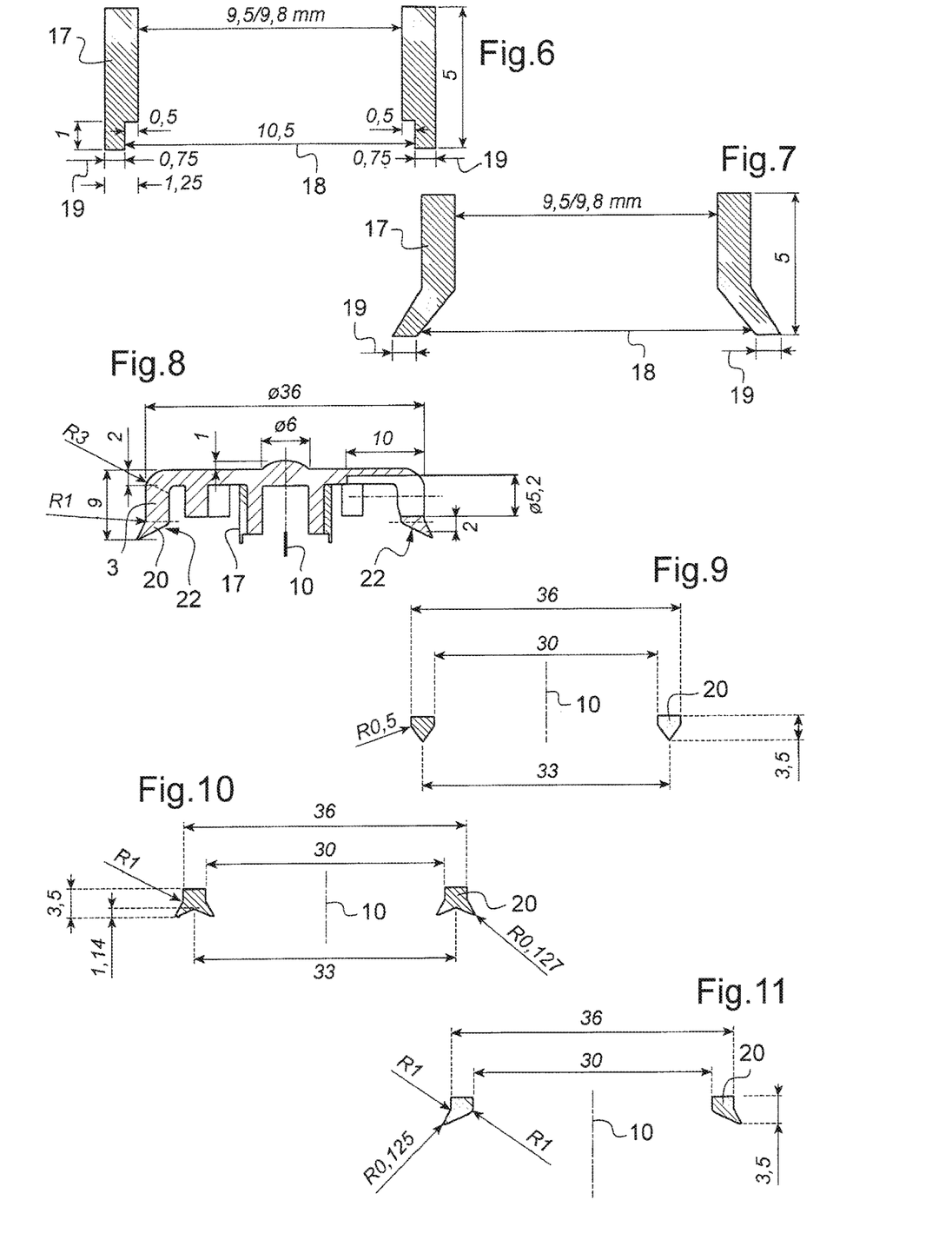

The ring 17 has:

a cylindrical shape, as shown in FIG. 6, or a cylindrical shape on the side of the back wall 5 and flared in the direction of the zone 4, as shown in FIG. 7.

The ring has rotational symmetry about axis 10.

Thus, it is possible to alter:

the diameter 18 of the hollow interior 13 on the side of the zone 4, and/or the area 19 of contact between the ring 17 and the tissue 8, as a function of the model of ring 17 selected for surrounding the stud 11.

The ring 17 improves the holding and closure of the wound.

The hollow stud can be provided with microstructured teeth.

The ring 17 is provided with microstructured teeth.

A description will now be given, with reference to FIGS. 8 to 11, of an additional piece in a variant of the first or second embodiment of the device according to the invention.

In this variant of the first or second embodiment of the device according to the invention, the peripheral supporting means 3 are arranged for receiving an additional piece 20 for altering the surface area of the plate or for modifying its profile.

The additional piece is fixed on the peripheral supporting means by bonding, clipping or by surface adhesion for example of two smooth surfaces of rubber that can be stuck together and unstuck a great many times.

Thus, the properties of adhesion and holding of the device 1, 16 to the tissue 8 can be modified and "tailored".

The additional piece 20 is provided with microstructured teeth 22 directed towards the tissue 8 and arranged to be in contact with the tissue 8 when the vacuum is created in the space 6. The additional piece 20 ensures better holding of the device on the tissue 8, by attachment of tooth-shaped microstructures 22 on the tissue 8.

A description will now be given, with reference to FIGS. 12 and 13, of a skirt for any one of the variant embodiments of the device according to the invention just described.

Figure 12:
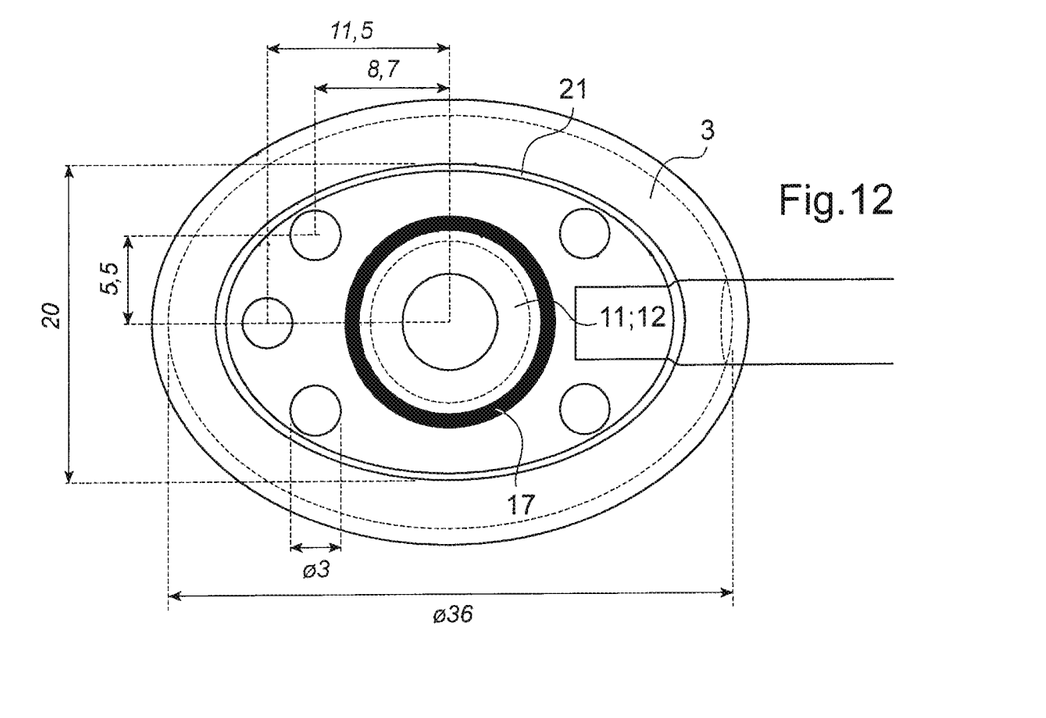
FIG. 12 is a bottom view of an embodiment of the device according to the invention equipped with a "skirt"
Figure 13:
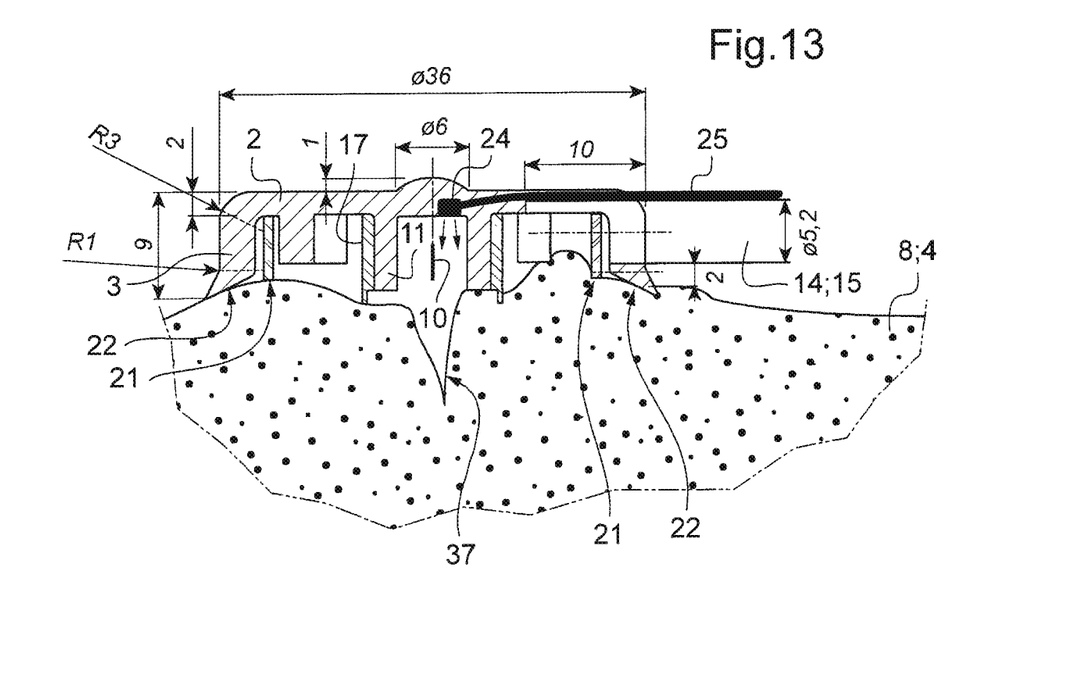
FIG. 13 is a profile sectional view of this embodiment of the device according to the invention equipped with a "skirt"

Any one of the variant embodiments of the device according to the invention can further comprise, as shown in FIGS. 12 and 13, a detachable skirt 21 placed between the peripheral supporting means 3 and the hollow stud 11, surrounding hollow stud 11, and arranged to be in contact with the tissue 8 when the vacuum is created in the space 6.

The skirt 21 is centered on the back wall 5.

The skirt ensures better holding of the device on the tissue 8.

Moreover, the device 1, 16 can incorporate a camera 24 for aiding the practitioner in positioning the plate 2 on the zone 4 and centring the plate 2 relative to the wound 37.

The camera is arranged for imaging the tissue via the hollow interior 23 when the hollowed-out side of the stud 11 is in contact with the zone 4.

A cable 25 connects the camera 24 to remote means (not shown) for receiving visual data from the camera.

The camera is supplied with power locally (cell, battery) or via the cable 25.

The cable starts from the camera 24 to the connecting means 14 and then follows the path of the duct 15.

The camera is offset relative to the central axis 10 of the stud 11, to allow a syringe to pierce the plate 2 for injecting a product into the hollow interior 13 without risk of damaging the camera 24 or the cable 25. Advantageously, so that there are no doubts about the position of the camera 24 and of the cable, the camera is displaced towards the connecting means 14.

A description will now be given, with reference to FIGS. 17 to 20, of a third embodiment of the device "A3" (referenced 38 in the figures) according to the invention called device "with central aspiration", only with respect to its differences relative to the first embodiment.

In this embodiment 38, the studs 9 are non-slip studs.

Moreover, in this embodiment 38, the connecting means 14 lead directly into the hollow stud 11, in the base of the hollow stud.

More precisely, the connecting means 14 lead into the hollow stud 11 via the top of the hollow stud on the side of the back wall 5.

Figure 17:
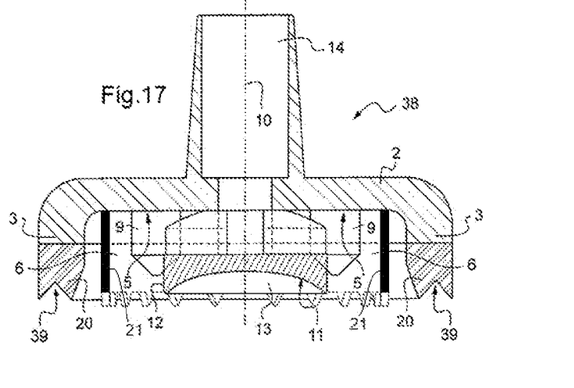
FIG. 17 is a profile sectional view of another embodiment of the device according to the invention called device "with central aspiration"
Figure 18:
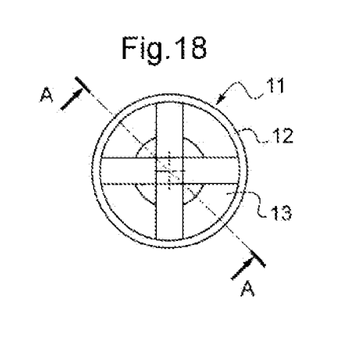
FIG. 18 is a bottom view of the hollow stud 11 of the embodiment "with central aspiration"

The fact that there is central aspiration, via the hollow stud 11, rather than lateral directly in the space 6:
avoids blocking the aspiration of the tissue 8, and
makes the aspiration more uniform.

Figure 19:
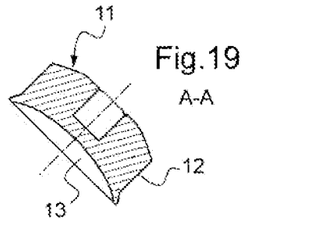
FIG. 19 is a profile sectional view of the hollow stud 11 of the embodiment "with central aspiration", along section A-A of FIG. 18.

Note that the hollow interior 13 has a concave interior shape.

In this embodiment 38, the hollow stud 11 has a dual function:
function of uniform distribution of the aspiration, and
function of stiffening the device by serving as a "pillar".

Figure 20:
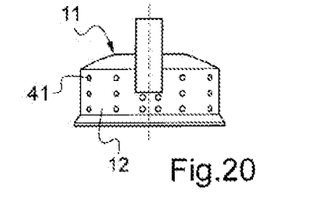
FIG. 20 is a profile view of the hollow stud 11 of the embodiment "with central aspiration"

In this embodiment 38, the wall 12 is perforated (holes 41) to allow the aspiration to be transmitted between the interior 13 of the stud 11 and the space 6.

The connecting means 14 lead into the hollow stud 11 with a cross-shaped hole (depicted in FIG. 18) so as to improve the negative pressure and its uniform distribution.

As with the embodiments described above, embodiment 38 can be equipped:

with the ring 17 or rigid metal ring (not shown), which will then be perforated to allow the aspiration to be transmitted between the interior 13 of the stud 11 and the space 6, and/or
with the additional piece 20, and/or
with the skirt 21 (not shown).

In a preferred variant of any one of the embodiments described above, the device according to the invention comprises a silicone part suitable for applying on biological tissue 8 and of different hardness, less than the hardness of the back wall 5.

It is known that there are Shore scales A, B, C, D, 0, and 00.

In this document, all the Shore values are given by default in the Shore A scale, unless stated otherwise.

The function of the back wall 5 is to provide the device with sufficient rigidity to withstand the negative pressure due to aspiration. The back wall has a hardness between 35 and 85 Shore A, preferably approximately equal to 50 Shore A.

The function of the part suitable for application on the biological tissue is to adapt to the shape of the wound or of the tissue 8. This part suitable for application on the biological tissue and with hardness different from the hardness of the back wall has a hardness between 0 and 50 Shore A, preferably approximately equal to 35 Shore A.

The part suitable for application on the biological tissue 8 and with hardness different from the hardness of the back wall comprises:
peripheral supporting means 3 made of silicone, and/or
the additional piece 20 made of silicone, if the device according to the invention is equipped with said additional piece.

Figure 21:
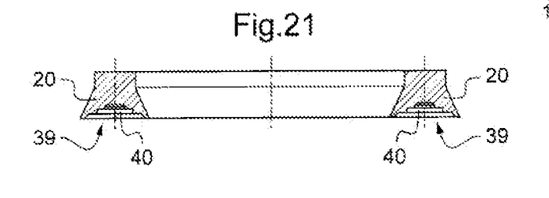
FIG. 21 is a profile sectional view of a variant of additional piece 20 for any one of the embodiments of device according to the invention.

With reference to FIG. 21, if the device according to the invention is equipped with the additional piece 20, the additional piece 20 is equipped with an intermediate seal 40 of silicone with hardness lower than the hardness of the additional piece 20 and placed so as to be situated between the additional piece 20 and the biological tissue. This allows it to adapt even better to the shape of the wound or of the tissue 8. The additional piece 20 is equipped with a slit 39 in the form of a closed loop and arranged for receiving the seal 40. The seal 40 has a hardness between 0 and 10 Shore 00 (i.e. on the Shore 00 scale), preferably approximately equal to 5 Shore 00.

A description will now be given, with reference to FIGS. 14 to 16, of another embodiment of the invention "B" (referenced 23 in the figures) which can be the subject of a divisional application, still in the area of plates for hemostasis.

Figure 14:
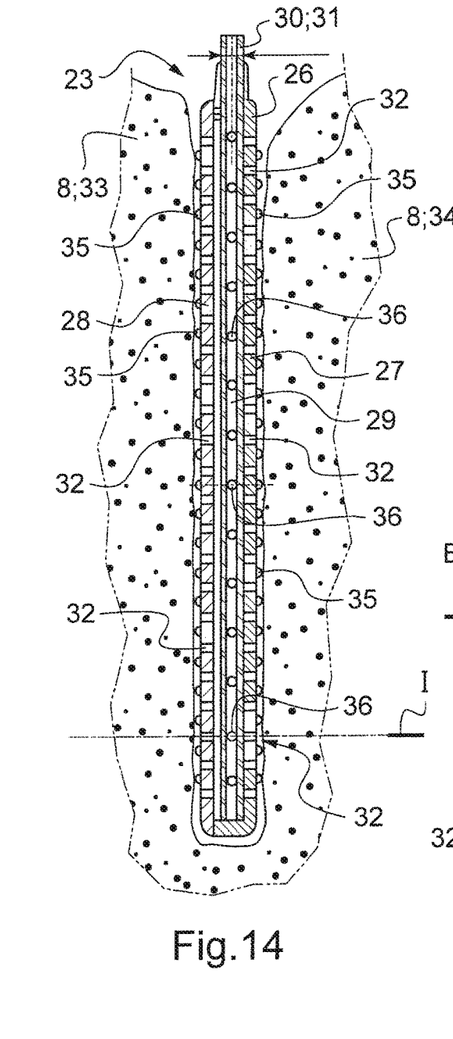
FIG. 14 is a profile sectional view of another embodiment of the device according to the invention called "plate for hollow organs"
Figure 15:
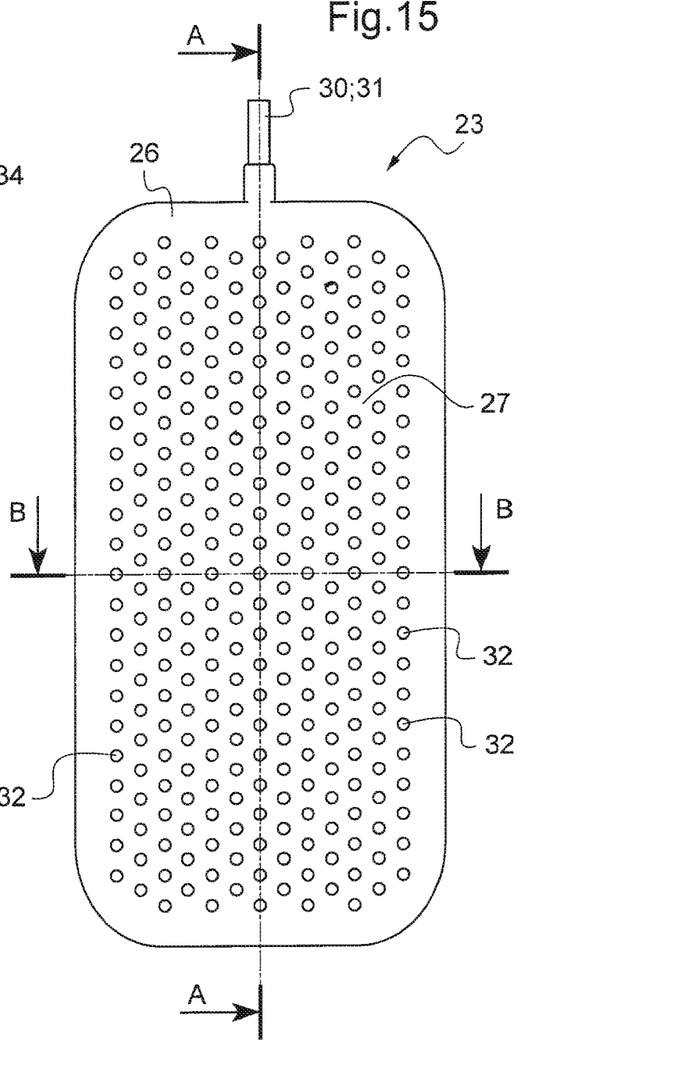
FIG. 15 is a top view of the "plate for hollow organs"

FIG. 14 is a profile sectional view along axis A-A of FIG. 15.

Figure 16:
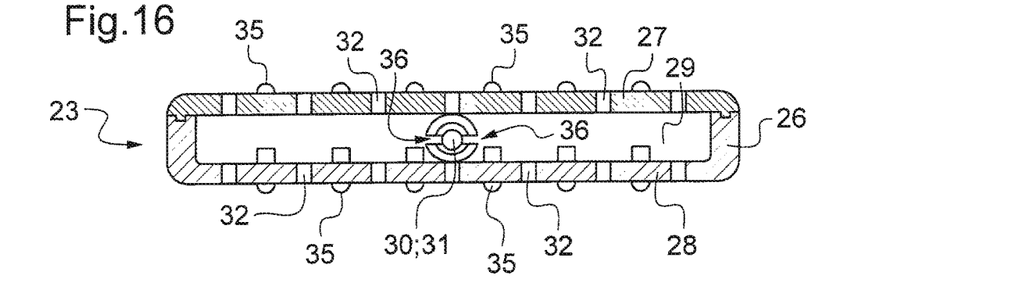
FIG. 16 is a front sectional view of the "plate for hollow organs"

FIG. 16 is a profile sectional view along axis I of FIG. 14.

FIG. 3 is a profile sectional view along axis II of FIG. 4.

The device 23 comprises:
a flat flexible plate 26 provided with two substantially parallel, opposite faces 27, 28, said plate comprising an internal volume 29 between its two faces, and
connecting means 30 arranged for connecting the internal volume 29 to aspirating means (not shown) external to said device so as to create negative pressure in this internal volume 29, said connecting means typically comprising a connecting tube 31
each of the faces 27, 28 being provided with holes 32 so that the internal volume 29 and the exterior of the plate communicate via these faces 27, 28.

Thus, the device can communicate the aspiration to the tissue 8 simultaneously via the two opposite faces 27, 28, and thus makes it possible to keep two opposite walls 33, 34 of a "hollow" organ, for example stomach or esophagus, close together, or preferably of the uterus in the case of hemorrhages that may occur during delivery in childbirth, in the internal wall of the patient's uterus.

Moreover, each of the faces 27, 28 of plate 23 is equipped, towards the exterior of device 23, with relief patterns 35 in the form of bumps.

The patterns 25 are evenly distributed on the faces 27, 28, with a substantially constant surface density. In the interests of clarity, these patterns are not shown in FIG. 15.

The role of these patterns 35 is to improve the hermeticity of the device 23 at the various sites of bleeding.

The tube 31 extends inside the volume 29, over the whole length of the volume 29.

This tube is provided, on its entire length within space 29, with pairs of lateral holes 36 so that the interior of tube 31 communicates with the volume 29, so that the negative pressure is properly uniform within the space 29.

Device "B" (referenced 23 in the figures) can for example be used:

in the case of hemorrhages or suppressed bleeding that may occur during delivery in childbirth, in the inside wall of the patient's uterus, when the latter is relatively atonic, especially in the region of placental insertion which can no longer be located precisely in the period following delivery and expulsion of the placenta.

Of course, the invention is not limited to the examples that have just been described and numerous adjustments can be made to these examples while remaining within the scope of the invention.

The invention claimed is:

1. A hemostatic device for controlling a blood flow occurring in a natural cavity of a uterus of a patient's body, the device comprising:
    a flat flexible plate provided with two substantially parallel, opposite faces, said plate comprising an empty internal volume between the two faces,
    the flat flexible plate being configured to be put on a hemorrhagic zone within the natural cavity of the patient's uterus; and
    connecting means arranged for connecting the empty internal volume to aspirating means external to said device so as to create a negative pressure in the empty internal volume,
    wherein each of the two faces defines a sucker provided with holes configured so that the empty internal volume and an exterior of the flat flexible plate communicate via the two faces, each sucker having an area configured such that when the negative pressure is created in the empty internal volume, opposite walls of the patient's uterus are held close together by aspiration via the holes of the opposite faces of the flat flexible plate,
    wherein the negative pressure created in the empty internal volume holding the opposite walls of the patient's uterus close together, by aspiration via the holes of the opposite faces of the flat flexible plate, is configured to stop or reduce bleeding in the patient's uterus by attracting and holding tissue of the patient's uterus against the sucker of each flat flexible plate.

2. The device of claim 1, wherein each of the faces is equipped, towards the exterior of the flat flexible plate, with relief patterns in the form of bumps.

3. The device of claim 2, wherein the relief patterns are evenly distributed on the faces, with a substantially constant surface density.

4. The device of claim 1, wherein said connecting means comprising a connecting tube extending inside the internal volume, over the whole length of the volume.

5. The device of claim 4, wherein the connecting tube is provided, on its entire length within the internal volume, with pairs of lateral holes so that the interior of the connecting tube communicates with the internal volume, so that the negative pressure is properly uniform within the internal volume.

6. The device of claim 1, wherein the uterus means the inside wall of the patient's uterus.

7. The device of claim 6, wherein the inside wall of the patient's uterus means the region of placental insertion.

* * * * *